(12) United States Patent
Rangarajan et al.

(10) Patent No.: US 6,704,101 B1
(45) Date of Patent: Mar. 9, 2004

(54) SCATTEROMETRY BASED MEASUREMENTS OF A MOVING SUBSTRATE

(75) Inventors: Bharath Rangarajan, Santa Clara, CA (US); Bhanwar Singh, Morgan Hill, CA (US); Ramkumar Subramanian, Sunnyvale, CA (US); Michael K. Templeton, Atherton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 33 days.

(21) Appl. No.: 10/050,423

(22) Filed: Jan. 16, 2002

(51) Int. Cl.$^7$ ................................................ G01N 21/00
(52) U.S. Cl. .................... 356/237.2; 356/630; 356/399
(58) Field of Search ...................... 356/237.1, 237.2, 356/237.3, 237.4, 237.5, 237.6, 630–632, 399–401; 359/196, 198, 201, 202, 225, 226; 250/559.3, 559.39, 559.45

(56) References Cited

U.S. PATENT DOCUMENTS

| | | | | | |
|---|---|---|---|---|---|
| 4,241,257 A | * | 12/1980 | Koester | ...................... | 250/235 |
| 4,627,734 A | * | 12/1986 | Rioux | ......................... | 356/607 |
| 5,432,607 A | * | 7/1995 | Taubenblatt | ................. | 356/364 |
| 5,625,193 A | * | 4/1997 | Broude et al. | .............. | 250/372 |
| 5,672,885 A | * | 9/1997 | Allen et al. | .............. | 250/559.3 |
| 6,201,601 B1 | * | 3/2001 | Vaez-Iravani et al. | ... | 356/237.4 |

* cited by examiner

Primary Examiner—Hoa Q. Pham
(74) Attorney, Agent, or Firm—Amin & Turocy, LLP

(57) ABSTRACT

A system and method are disclosed for monitoring characteristics of a substrate. A substrate is supported for movement within a processing environment and an incident light beam is emitted onto a surface of the substrate. The incident beam is provided to a moveable reflector that directs the beam to the substrate. A control system controls movement of the reflector so as to selectively interrogates the substrate with the beam.

23 Claims, 5 Drawing Sheets

SCATTEROMETRY BASED MEASUREMENTS OF A MOVING SUBSTRATE

TECHNICAL FIELD

The present invention relates to semiconductor processing and, more particularly, to a system and method for monitoring characteristics of a moving substrate.

BACKGROUND

In the semiconductor industry, there is a continuing trend toward higher device densities. To achieve these higher densities, efforts continue toward scaling down device dimensions (e.g., at sub-micron levels) on semiconductor wafers. To accomplish such high device packing densities, smaller and smaller feature sizes are required. This may include the width and spacing of interconnecting lines, spacing and diameter of contact holes, and the surface geometry such as comers and edges of various features.

The process of manufacturing semiconductors, or integrated circuits, typically consists of more than a hundred steps, during which numerous of copies of an integrated circuit may be formed on a single wafer. Generally, the process involves creating several patterned layers on and into the substrate that ultimately form the complete integrated circuit. Fabricating a semiconductor using such sophisticated manufacturing techniques may involve a series of steps including cleaning, thermal oxidation or deposition, masking, etching, and doping.

Wafers may be pre-cleaned using, for example, high-purity, low-particle chemicals. Silicon wafers may be heated and exposed to ultra-pure oxygen in diffusion furnaces under carefully controlled conditions to form a silicon dioxide film of uniform thickness on the surface of the wafer.

A masking step is utilized to protect one area of the wafer while working on another area. This process typically includes photolithography or photo-masking. A photoresist or light-sensitive film is applied to the wafer, such as while supported in a suitable spin coating apparatus. A photo-aligner aligns the wafer to a mask and then projects an intense light through the mask and through a series of reducing lenses, exposing the photoresist with the mask pattern.

The wafer is then "developed" (the exposed photoresist is removed), such as by applying a developing solution while rotating the substrate on a suitable support. The developed substrate may then be thermally baked to harden the remaining photoresist pattern. It is then exposed to a chemical solution or plasma (gas discharge) so that areas not covered by the hardened photoresist may be etched away. The photoresist is removed using additional chemicals or plasma. In order to ensure correct image transfer from the mask to the top layer, various wafer inspection methodologies may be employed.

In a doping step, atoms with one less electron than silicon (e.g., boron), or one more electron than silicon (e.g., phosphorous), are introduced into the area exposed by the etching process to alter the electrical character of the silicon. These areas are called P-type (boron) or N-type (phosphorous) to reflect their conducting characteristics. The thermal oxidation, masking, etching and doping steps may be repeated several times until the last "front end" layer is completed (e.g., all active devices have been formed).

Following completion of the "front end," a metalization process is implemented in which the individual devices are interconnected using a series of metal depositions and patterning steps of dielectric films (insulators). Semiconductor fabrication may include one or more metal layers separated by dielectric layers. Openings are etched in this film to allow access to the top layer of metal by electrical probes and wire bonds.

As device densities continue to improve, it becomes increasingly important in the semiconductor fabrication process to monitor feature characteristics at various stages of the process. In particular, it has become desirable to monitor characteristics while the substrate is moving, such as during fabrication (e.g., associated with a deposition, etching process, or the like).

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides a system and method for monitoring characteristics of a substrate. A positioning system supports a substrate for movement. A measurement system emits a beam onto a moveable reflector, which reflects an incident beam to the substrate. The measurement system also detects a reflected and/or diffracted beam from the substrate. A control system controls movement of the reflector based on movement of the support to facilitate selective interrogation of the substrate.

In a particular aspect, the support moves the substrate (e.g., rotational movement) within a processing environment in which a desired material is applied to or removed from the substrate. The detected reflected and/or diffracted beam has optical properties indicative of substrate characteristics, such as thickness of a layer (or layers) of materials formed on the substrate. Accordingly, the application of materials onto the substrate and/or other process parameters can be controlled based on the optical properties of the reflected and/or diffracted beam.

Another aspect of the present invention provides a method for measuring characteristics of a substrate. The method includes moving a substrate supported within a processing environment. An incident light beam is emitted onto a reflector as the orientation of the reflector is adjusted based substrate movement so that the beam can selectively interrogate a surface of the substrate. Reflected and/or diffracted light is provided in response to interaction of the incident beam with the substrate, which reflected and/or diffracted light has optical properties indicative of substrate characteristics.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents.

Other advantages and novel features of the invention will become apparent from the following detailed description of the invention when considered in conjunction with the drawings.

DETAILED DESCRIPTION

The present invention provides a system and method for monitoring characteristics of a substrate. The substrate may be supported on a moveable support, such as adapted to rotate the substrate during fabrication. A measuring system is operable to emit an incident beam on to a reflector operable to direct the beam onto a selected part of the moving substrate. The incident beam thus interacts with the selected part of substrate and provides a diffracted and/or reflected beam(s). The diffracted and/or reflected beam(s) can be analyzed to determine substrate characteristics. In order to facilitate interrogating the selected part of the substrate, the reflection system can be positioned as a function of the position and/or rotation of the moveable support in accordance with an aspect of the present invention. As a result, the beam is able to selectively interrogate the substrate, thereby mitigating errors due to rotation of the substrate and still providing useful information about the process and the substrate.

Figure 1:
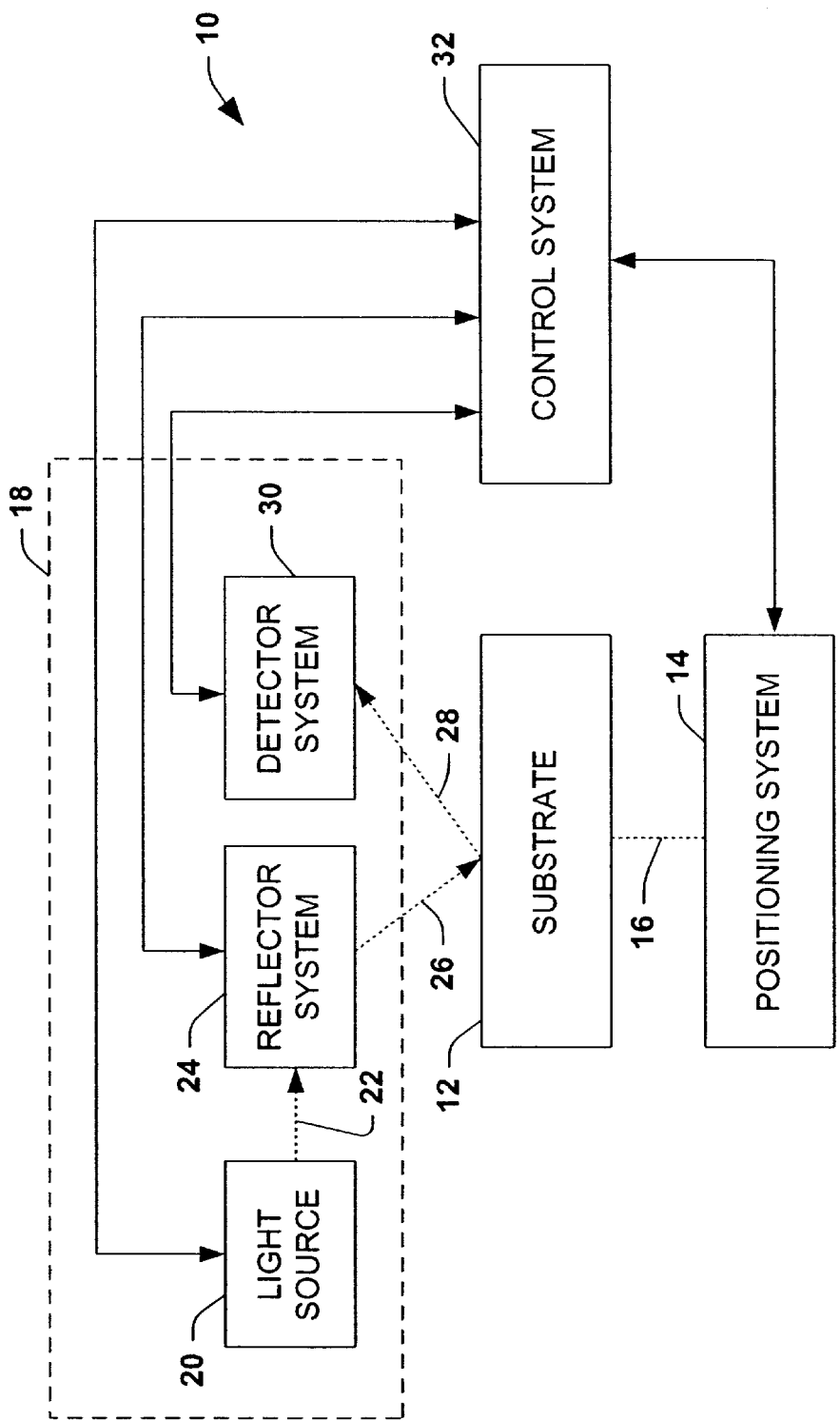
FIG. 1 is a simplified block diagram of a monitoring system in accordance with an aspect of the present invention.

FIG. 1 illustrates a block diagram of a measuring system 10 operative to measure characteristics of a substrate 12 in accordance with an aspect of the present invention. The substrate 12 is operatively connected to a positioning system 14 through a moveable support (e.g., a chuck and stage), schematically indicated at 16. By way of example, the positioning system 14 is operative to rotate the support 16 on which the substrate 12 is positioned, which, in turn, causes the substrate also to rotate. The substrate 12, for example, can be vacuum absorbed or otherwise fixed relative to the support to enable its rotation with the support. The rotation of the substrate 12 may be in connection with one or more processing steps, such as, for example, spin coating or developing and the like.

The system 10 also includes a measurement system 18 operable to measure characteristics of the substrate 12, in accordance with an aspect of the present invention, including when the positioning system 14 rotates the substrate. The measurement system 18, for example, includes a light source 20 that emits an incident beam 22 on to a moveable reflector system 24. The reflector system 24 is controlled to position a mirror, such that a reflected beam 26 is directed on to a selected part of the substrate. In one aspect, the reflector system 24 can move the mirror to align the reflected beam 26 to strike a particular part of the substrate 12 as it rotates. That is, the position of the mirror can be controlled as a function of substrate position so that the reflected beam 26 excites a known part of the substrate. The beam 26 interacts with the substrate 12 and is diffracted and/or reflected as beam 28.

The measurement system 18 also includes a detector system 30, such as a spectrometer, for detecting the diffracted and/or reflected light beam 28 from the substrate 12. Characteristics of the substrate 12 are determined based on the properties of the diffracted and/or reflected beam 20. The beam 28 further can be routed from the substrate to a detector device, such as a spectrometer, by another moveable reflector system similar to the system 24, although other optical networks could be configured to route the diffracted and/or reflected beam accordingly.

Alternatively, the incident beam 26 can pass through the substrate, in which case the detector system would be located at the opposite side of the substrate 12 relative to the reflector system 24. Those skilled in the art will understand and appreciate various non-destructive optical measurement techniques that could be utilized in accordance with an aspect of the present invention.

The system 10 includes a control system 32 operatively coupled to the positioning system 14 and the measurement system 18, such as including the light source 20, the reflector system 24, and the detector system 30 thereof. The control system 32 is programmed and/or configured to control operation of the positioning system 14 and the measurement system 18 in accordance with an aspect of the present invention.

According to one particular aspect, the control system 32 is programmed to control the position of the reflector system 24 as a function of the position and/or movement (e.g., rotation) of the substrate 12. Specifically, the control system 32 receives information from the positioning system 14 indicative of the position and/or velocity of the substrate. Because the substrate position is known and substantially fixed relative to the position of the support, which is being moved by the positioning system 14, the position of the substrate 12 can be determined from position and/or velocity information obtained from the positioning system 14 (or an associated encoding system). Consequently, the control system 32 can employ the rotation information to control operation of the measurement system 18 so that the reflector system 24 emits the beam to selectively interrogate a given location (or locations) on the substrate 12. Additionally, the light source can emit the beam 22 in a pulsed fashion to selectively interrogate different parts or gratings of the substrate. As mentioned above, the detector system 30 can include another reflector that can be moved as a function of the position or movement of the substrate to collect and the reflected and/or diffracted beam 28 and, in turn reflect the beam to an associated light sensing system that forms part of the detector system (e.g., a spectrometer).

Alternatively or additionally, the control system 32 can be programmed and/or configured to implement an interdependent control of the positioning system 14 and the measurement system 18, such that beam emission and reflection are synchronized with the rotation of the substrate 12, as provided by the positioning system. For example, a mirror of the reflector system 24 can move about one or more axes. The movement of the mirror is determined as a function of feedback from the reflector system 24 indicative of reflector movement and/or feedback from the positioning system 14 indicative of substrate movement. As a result, the beam 26 can be directed to excite a determined spot on the substrate so as to obtain desired topographical information about the part of the substrate where the beam 26 strikes.

Figure 2:
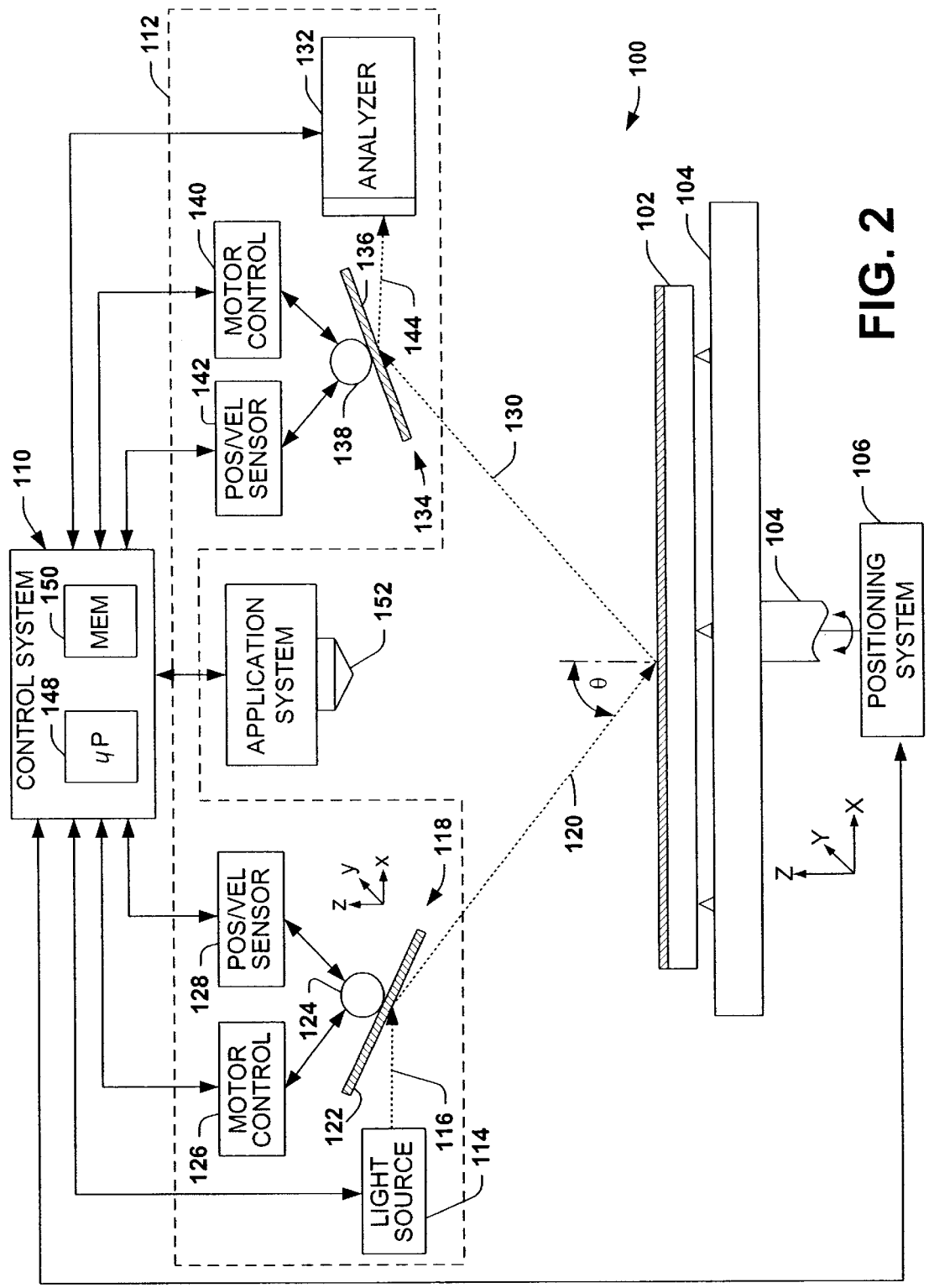
FIG. 2 is a schematic block diagram of a monitoring system in accordance with an aspect of the present invention.

FIG. 2 illustrates another example of a system 100 for measuring characteristics of a substrate 102 in accordance with an aspect of the present invention. In this example, the substrate 102 is supported by a moveable support 104, such as a chuck. The support 104 is operatively connected to a positioning system 106. The positioning system 106 can be operable to move the support 104 in one or more directions, such as the x, y, and/or z-directions. In addition, the positioning system 106 includes a suitable servomotor (not shown) for rotating the support 104 and the substrate 102 located thereon about the z-axis. The support 104 also can include a vacuum chuck operative to hold the substrate 102 at a desired fixed position relative to the support.

By way of further illustration, the substrate 102 can include one or more alignment markers, which are utilized to position the substrate at a predefined position relative to the upper surface of the support 104. The upper surface of the support 104 can include corresponding marks to facilitate such positioning. The positioning system 106 includes a position sensing device, such as one or more encoders (e.g., optical, magnetic, hall effect, etc.), which is employed to provide a signal having information indicative of the position of the support 104. The position information can include rotary position about a central axis (the Z-axis), as well as positions in mutually orthogonal axes along which the support 104 can move. Because the substrate 120 is at a known fixed position relative to the support 104, the absolute position of the substrate can be readily discerned from the encoder data.

The substrate 102 is rotated, for example, to facilitate application of resist coating (e.g., in spin coating system) or the application of a suitable solvent material (e.g., in a developer) onto the surface of the substrate. The positioning system 106 controls the rate of rotation of the support 104, which can vary according to the process being implemented within the processing environment. For example, it may be desirable to rotate the support at a substantially fixed rate or it may be desirable to selectively adjust the rotation rate (e.g., accelerate or decelerate), such as at different stages of an associated fabrication process. The positioning system 106 is coupled to a control system 110. The control system 110 thus can receive position and/or velocity information from the positioning system as well as control operation of the positioning system to adjust the position of the support 104 and the substrate 102 positioned thereon.

The system 100 also includes a measuring system 112 for measuring topographical features of the substrate 102 in accordance with an aspect of the present invention. The control system 110 is coupled to the measurement system 112 for controlling operation thereof as well as for obtaining information indicative of the parameters measured by the measurement system.

By way of illustration, the measuring system 112 includes a source of light 114, such as one or more optical emitters, for emitting a light beam 116 toward a reflector system 118. The light source 114 is coupled to the control system 110, such that the control system can control operation of the light source. The light source 114 can be a frequency stabilized laser however it will be appreciated by one skilled in the art that any laser or other light source (e.g., laser diode, or helium neon (HeNe) gas laser, halogen lamp, etc.) suitable for carrying out the present invention may be utilized. The reflector system 118 reflects the beam 116 as an incident beam 120 toward the substrate 102. The incident beam 120 strikes the substrate 102 at an angle of incidence, indicated at θ, relative to a normal reference line.

In accordance with an aspect of the present invention, the reflector 118 includes a mirror 122 that is moveable about one or more axes (e.g., x-axis, y-axis, and/or z-axis). For example, the mirror 122 can have a substantially planar or curved reflective surface. The mirror 122 is operatively connected to a motor 12, which can be operative to effect movement (or rotation) of the mirror about one or more axes. The motor 124 is coupled to a motor controller 126 and to a position and/or velocity sensor 128 (hereinafter referred to as the "position sensor 128" for sake of brevity).

The motor controller 126 and position sensor 128 are coupled to the control system 110. The motor controller 126, for example, includes an amplifier and switching circuit configured to selectively activate the motor 124 to adjust the position of the mirror 122 relative to one or more axes based on a control signal from the control system 110. The motor 124 thus can include one or more high resolution servo motors operative to effect rotation of the mirror 122 about such axes. The position sensor 128 is operatively associated with the motor 124 to sense position and/or velocity of the motor. The position sensor 128 provides a signal to the control system 110 indicative of the sensed position and/or velocity.

The control system 110 employs the position signal to determine control parameters for the motor controller 126 based on the position information obtained from the positioning system. That is, the control system 110 controls the position of the mirror 122 based on the position feedback information from the position sensor 128 and the position feedback from the positioning system 106, which corresponds to the position of the substrate 102. By way of example, the control system 110 is programmed and/or configured to adjust the position of the mirror 122 about one or more of its axes to selectively interrogate (or excite) a desired part of the substrate 102. That is, the movement of mirror 122 can be synchronized with movement of the substrate 102 so that the incident beam 120 is reflected from the mirror onto a selected grating or part of the substrate as the substrate rotates. After a suitable measurement is obtained for the selected part of the substrate, as described below, the control system 110 can adjust operating parameters of the motor 124 to interrogate a next part of the substrate. This process can be repeated to obtain information about different parts of the substrate, such as according to preprogrammed recipe.

The incident beam 120 interacts with the substrate 102 to diffract a portion of the incident beam, thus producing a diffracted and/or reflected beam 130. The measuring system 112 also includes an analyzer 132 for detecting optical characteristics of the reflected light beam 130. The analyzer 132 is programmed and/or configured to discern optical characteristics of the substrate 102 based on the optical properties of the beam 130. The optical characteristics of the substrate 102 further provide information about the topographical characteristics of the substrate.

The topographical characteristics, for example, can include feature characteristics and/or defects, voids, thickness of layers, and may be determined based on the spectral content (wavelength) and/or the intensity of the reflected beam 130.

In the example of FIG. 2, the reflected beam 130 is received at a reflector system 134, which includes a mirror 136 operatively connected to a multi-axis motor 138. The motor 138 is coupled to a motor controller 140 and to a position and/or velocity sensor 142. The motor controller 140 and position and/or velocity sensor 142 are coupled to the control system 110. The operation of the motor 138 to adjust the position of the reflective surface of the mirror 136 is substantially similar to that described above with respect to the reflector 118.

Briefly stated, the control system 110 provides control information to the motor controller 140 to control the position of the mirror 136 based on the position and/or velocity information from the position sensor 142 and the rotation information from the positioning system 106. In particular, the mirror 136 is oriented to receive the reflected beam 130 and to route (or redirect) the beam as beam 144 to the analyzer 132. The control system 110 can be programmed and/or configured to synchronize movement (or position) of the mirrors 122 and 136 relative to each other, in accordance with an aspect of the present invention, such a given portion of the substrate 102 is interrogated by an incident beam 120 and the corresponding reflected beam 130 is routed to an analyzer 132.

By way of example, the analyzer 132 can include a spectrometer or any instrument that capable of providing spectrally-resolved information concerning the reflected beam 130, 144. The portion of the reflected beam 144 that enters the spectrometer for analysis varies as a function of substrate characteristics and its associated diffraction characteristics, the spectral characteristics of the incident beam, properties of the analyzer, and any associated optical elements that might be used in conjunction with the analyzer 132.

Examples of techniques that may be utilized in accordance with an aspect of the present invention include optical interference, ellipsometry, reflectometry, capacitance, and use of an associated color chart. Microprocessor controlled scatterometry or optical interference (e.g., microspectrophotometry) and spectroscopic ellipsometry are types of non-destructive optical measurement techniques that could be utilized in accordance with an aspect of the present invention.

The control system 110 is operatively coupled to the various components (114, 126, 128, 132, 140, 142) of the measuring system 118 and to the positioning system 106. The control system 110 receives the measured data from the analyzer 132 indicative of optical properties of the beam 144, as well as position and/or velocity data from the positioning system 106 and from the position sensors 128 and 142. The control system 110 is programmed and/or configured to determine topographical features associated with the substrate 102, such as may include feature properties, film thickness and/or defects, based on the analyzed measurement data received from the analyzer 132.

The control system 110 includes a processor 148 and memory 150. The processor 148 is programmed and/or configured to control and operate the various components within system 100 in order to carry out the various functions described herein. The processor 148 can be any of a plurality of commercially available or proprietary processors. The manner in which the processor 148 may be programmed to carry out the functions relating to the present invention will be readily apparent to those having ordinary skill in the art based on the description provided herein.

The memory 150 stores program code executed by the processor 148 for carrying out operating functions of the system 100. The memory 150 also serves as a storage medium for temporarily storing information, such as rotation/position information, wafer coordinate tables, scatterometry information, topographical features relative to wafer coordinates, and other data that may be employed in carrying out the present invention. The various components of the system 100 receive power from one or more power sources (not shown).

By way of illustration, the control system 110 provides control signals to the measuring system 60, including to the light source 114, the motor controllers 126 and 140 as well as to the positioning system 106 to synchronize their operation in accordance with an aspect of the present invention. In particular, the position of the substrate 102 and the mirrors 122 and 136 are controlled such that the incident beam 120 is emitted onto a selected portion of the substrate and the reflected beam 130 is routed to the analyzer 132, all in synchronization with the rotation of the substrate 102. Because the emission of the reflected incident beam 120, the collection of the reflected beam 130 and the rotation of the substrate 102 cooperate in this manner, different parts of the substrate can be selectively interrogated for analysis. As a result, errors associated with the measurements due to movement (e.g., rotation) of the substrate 102 during measuring are mitigated. This further facilitates in situ monitoring of the substrate and control of associated process parameters in accordance with an aspect of the present invention.

By way of further illustration, the system 100 may be implemented during fabrication, such as associated with application or removal of materials relative to the substrate 102. In the example of FIG. 2, the control system 110 also is coupled to an application system 152, which can apply material onto the substrate 102, such as resist coating, a developing solution, an etchant, etc.

For example, chemical deposition processes that can be utilized, in accordance with an aspect of the present invention, include Low Pressure CVD (LPCVD), Plasma Enhanced CVD (PECVD), and Rapid Thermal CVD (RTCVD). It is to be appreciated, however, that the present invention is applicable to other types of thin film formation, such as other deposition techniques (e.g., Physical Vapor Deposition (PVD), Metal Organic Chemical Vapor Deposition (MOCVD), Pulsed Laser Deposition (PLD)) and film growth techniques.

The application system 152 is operatively coupled to the control system 110 for receiving control information and/or providing feedback indicative of process conditions associated with the application of material. In addition, the control system 110 can adjust operating characteristics of the application system 110 based on the measurement data and/or the rotation data from the measuring system 118 and the positioning system 106. In a particular aspect, the control system 110 can collectively control operation of the measuring system 118, the positioning system 106, the application system 110, and/or other operating characteristics (e.g., substrate alignment, temperature, etc.) so as to improve the efficiency and/or accuracy of the various process steps being implemented. For example, the measurement system 118 can measure the thickness of materials being applied onto or being removed from the substrate in situ. As a result, the system 100 can be employed to adjust process parameters to facilitate or enhance application (or removal) of material relative to the substrate 102, even when the substrate is moving.

In accordance with a particular aspect of the present invention, scatterometry can be employed to extract information about the substrate 102 upon which an incident light 120 has been directed. One or more gratings may be located on a substrate. Such gratings may be formed on the substrate, for example, at the same stage in fabrication when alignment markers are formed thereon, such as by etching. Light reflected from, and/or passed through, the one or more gratings and/or features is collected by one or more light detecting components of the measurement system 118. It is to be appreciated that any suitable scatterometry system may be employed to carry out the present invention, and such systems are intended to fall within the scope of the claims.

By way of particular illustration, the measuring system 118 could be implemented as a broadband scatterometry system. In general, scatterometry is a technique for extracting information about a surface upon which an incident light has been directed. Information concerning properties including, but not limited to, dishing, erosion, profile, thickness of thin films and critical dimensions of features present on a surface such as a wafer can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties can include the chemical properties of the surface, the planarity of the surface, features on the surface, voids in the substrate, and the number and/or type of layers beneath the surface. In the present invention, the intensity and/or phase of the reflected and/or diffracted light may be examined as it relates to profiles of film thickness and/or gratings on the wafer being fabricated. The determined thickness measurements further can be employed as feedback during fabrication to adjust one or more operating parameters of an ongoing process.

In order to determine layer thickness, for example, the analyzer 132 (or control system 110) can employ measured signal characteristics to generate a signature based on the optical properties of the light 144. The generated signatures may be compared with a signal (signature) library of intensity/phase signatures to determine the desired characteristics of the moving substrate. Such substantially unique phase/intensity signatures are produced by light reflected from and/or refracted by different surfaces due, at least in part, to the complex index of refraction of the surface onto which the light is directed.

The signal (signature) library can be constructed from observed intensity/phase signatures and/or signatures generated by modeling and simulation. By way of illustration, when exposed to a first incident light of known intensity, wavelength and phase, a first feature on a wafer can generate a first component of a phase/intensity signature. Similarly, when exposed to the first incident light of known intensity, wavelength and phase, a second feature on a wafer can generate a second component of a phase/intensity signature. The components can be determined over a broadband range of wavelengths and aggregated to form a signature. For example, a particular type of thin film having a first thickness may generate a first signature while the same type of film having a different thickness may generate a second signature, which is different from the first signature.

Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing, for example, numerous phase/intensity signatures. Thus, when the phase/intensity signals are received from ellipsometry detecting components, the phase/intensity signals can be pattern matched, for example, to the library of signals to determine whether the signals correspond to a stored signature. Interpolation between the two closest matching signatures further may be employed to discern a more accurate indication of thickness from the signatures in the signature library. Alternatively, artificial intelligence techniques may be employed to calculate desired parameters of the wafer under test based on the detected optical properties.

According to another aspect of the invention, the present invention can employ spectroscopic ellipsometry to measure characteristics of the substrate 102. Ellipsometry is a nondestructive optical technique, which deals with the measurement and interpretation state of polarized light undergoing oblique reflection from a sample surface. The quantities measured by an ellipsometer are ellipsometric angles Psi (amplitude ratio) and Delta (phase changes) which are related to the complex ratio of the Fresnel reflection coefficient Rp and Rs for light polarized parallel (p) and perpendicular (s) to the plane of incidence such that $Rp/Rs = \tan(PSI)e^{iDELTA}$.

Ellipsometric data can be taken at multiple wavelengths (spectroscopic ellipsometry) and also at different angles of incidence. The experimental result of the spectroscopic variable angle of incidence ellipsometry measurements can be expressed as cos(Delta) and tan(Psi). These additional ellipsometric measurements provide much more information about the samples that can be obtained from a single wavelength and angle measurements. One type of spectroscopic ellipsometer is based on a mechanically rotating single polarizing element, polarizer or analyzer. Another type is based on phase modulation, where the polarizers are fixed and an additional element, the analyzer, performs the modulation function. It is to be appreciated that various types of spectroscopic ellipsometry techniques may be employed to carry out the present invention.

In another aspect of the invention a reflectometry technique can be employed to determine characteristics (e.g., film thickness, critical dimensions, defects, etc.) of a moving substrate. With a reflectometry technique, the light source emits the beam of light 130 at a fixed incident angle θ (e.g., about 90 degrees) relative to surface of the substrate 102. The spectral reflectivity of the substrate surface is modulated by optical interference. The effect of the interference on the measured spectrum is a function of the refractive indices of the substrate surface receiving the incident light 120. For example, if the wavelength of the beam 116 is varied, such as between a wavelength in the range of about 100–800 nm, and if the dispersion components of the refractive indices are known over the wavelength range, the thickness of the film being applied to the substrate 102 can be found using a Fourier transform technique. Other transformation techniques can be employed to carry out the present invention.

The intensity of the reflected light beam 144 can be measured as a function of its wavelength, with a minimal intensity being used to calculate various characteristics of the substrate 102, including film thickness. In accordance with an aspect of the present invention, the control system 110 controls the light source 114 and the position of the mirror 122 so as to selectively interrogate a given grating or different gratings at different locations on the substrate 102. The control system 110 also controls the position of the mirror 136 according to rotation of the substrate to provide the reflected beam 144 to the analyzer 132. The analyzer 132 thus can derive an indication of the optical properties associated with the reflected beam 144. The analyzer 132, in turn, provides an indication of the measured optical properties to the associated control system 110. The control system 110 further can control the measurement system and/or the positioning system 106 to synchronize their operation to mitigate errors that could be associated with measuring characteristics of the moving substrate 102.

By way of further example, when the measurement system 118 is implemented as part of a reflectivity system, it can employ pre-selected values for the index of refraction to facilitate calculating the thickness of the layers and other characteristics of the substrate based on the measured optical properties of the reflected beam relative to the incident beam 116. The information provided by the analyzer 132, for example, can include an indication of the thickness, such as based on analysis of the magnitude and phase of the beam 116 and reflected light beams 144. Alternatively, the analyzer 132 can provide raw data to the associated control system 110, which may employ such data to derive an indication of desired substrate characteristics.

Figure 4:
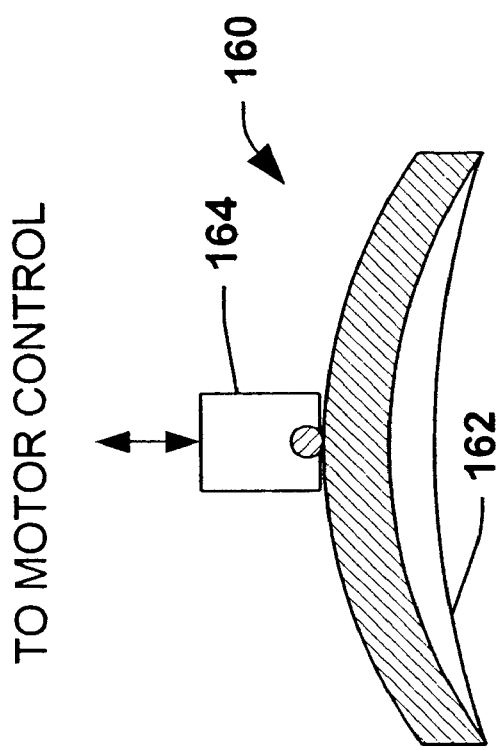
FIG. 4 is an example of the moveable reflector system taken along line 4—4 of FIG. 3.
Figure 3:
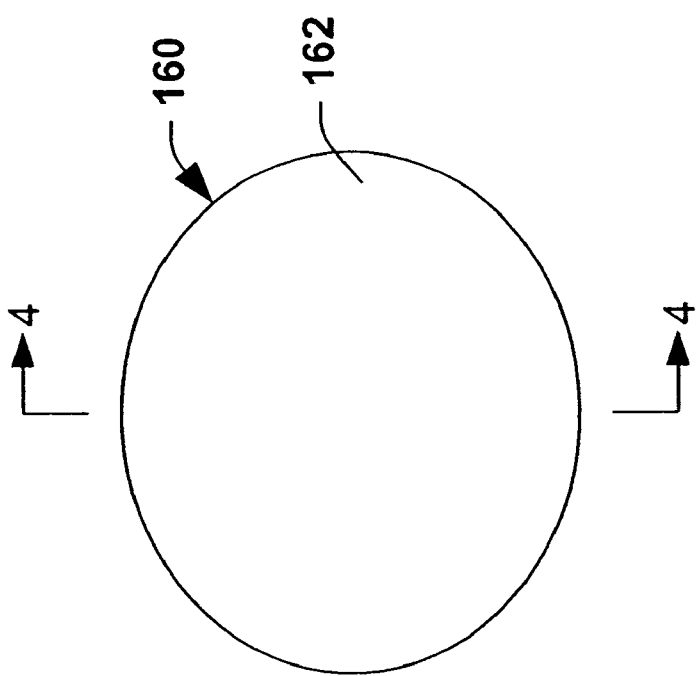
FIG. 3 is an example of a moveable reflector system that can be employed in accordance with an aspect of the present invention.

FIGS. 3 and 4 illustrate another example of a moveable reflector system 160 that can be utilized to direct light onto a substrate and or to an analyzer in accordance with an aspect of the present invention. That is, while the reflector in FIG. 2 is shown and described as having a mirror with a substantially planar reflective surface, it is to be understood and appreciated that the mirror alternatively could have a curved surface. FIGS. 3 and 4 illustrate a mirror 162 having a concave reflective surface, although it will be understood and appreciated that other configurations of curved mirrors and reflective surfaces also could be utilized in accordance with an aspect of the present invention. As shown in FIG. 4, a motor or other motive device 164 is connected to the mirror 162. The motor 164 communicates with a control system to effect desired movement of the mirror about one or more axes. The movement of the mirror 162 enables the mirror to reflect light received by the mirror in a selectable direction, such as toward a wafer or toward a light detector or analyzer, such as according to the application in which the mirror is being implemented.

Those skilled in the art will understand and appreciate various techniques and types of motive devices that can be utilized in accordance with an aspect of the present invention. For example, the motor could be implemented as one or more servo motors, an arrangement of piezoelectric actuators connected to move different parts of the mirror, and the like operative to adjust the position of the mirror to selectively direct the incident beam on to the substrate, as described herein.

Figure 5:
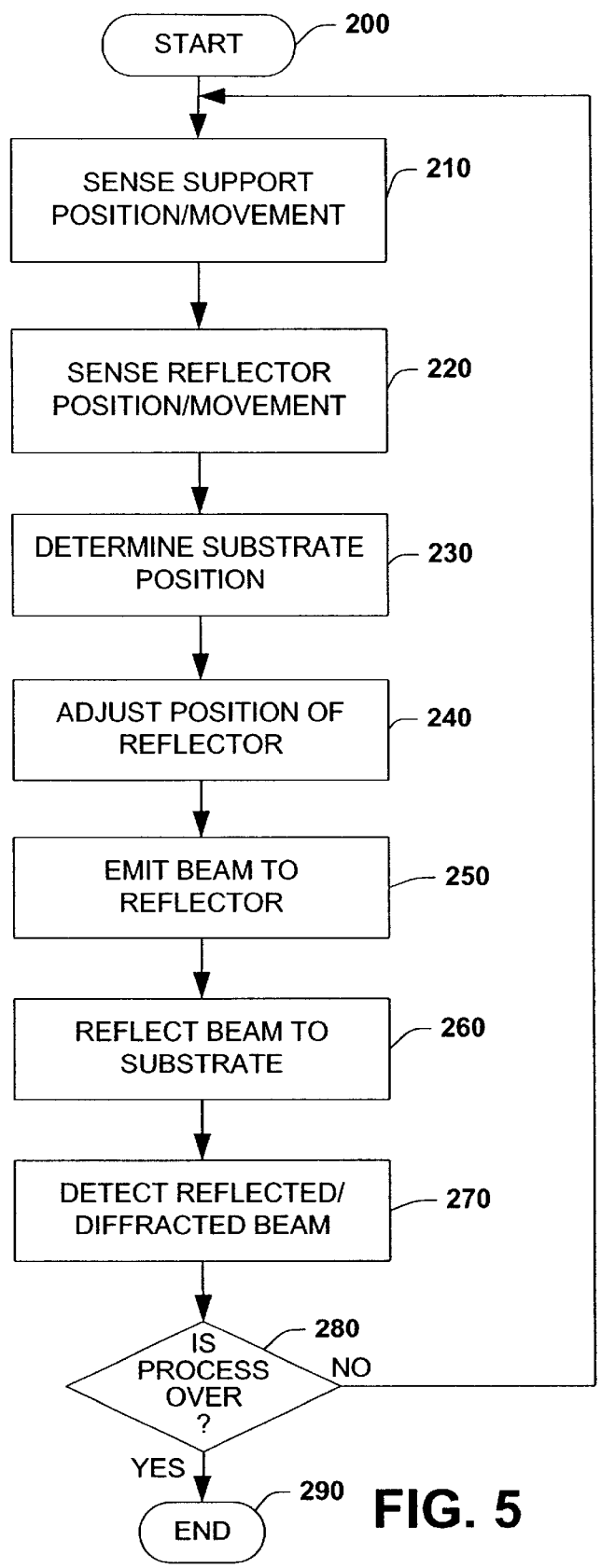
FIG. 5 is a flow diagram illustrating an example of a methodology for monitoring substrate characteristics in accordance with the present invention.
Figure 6:
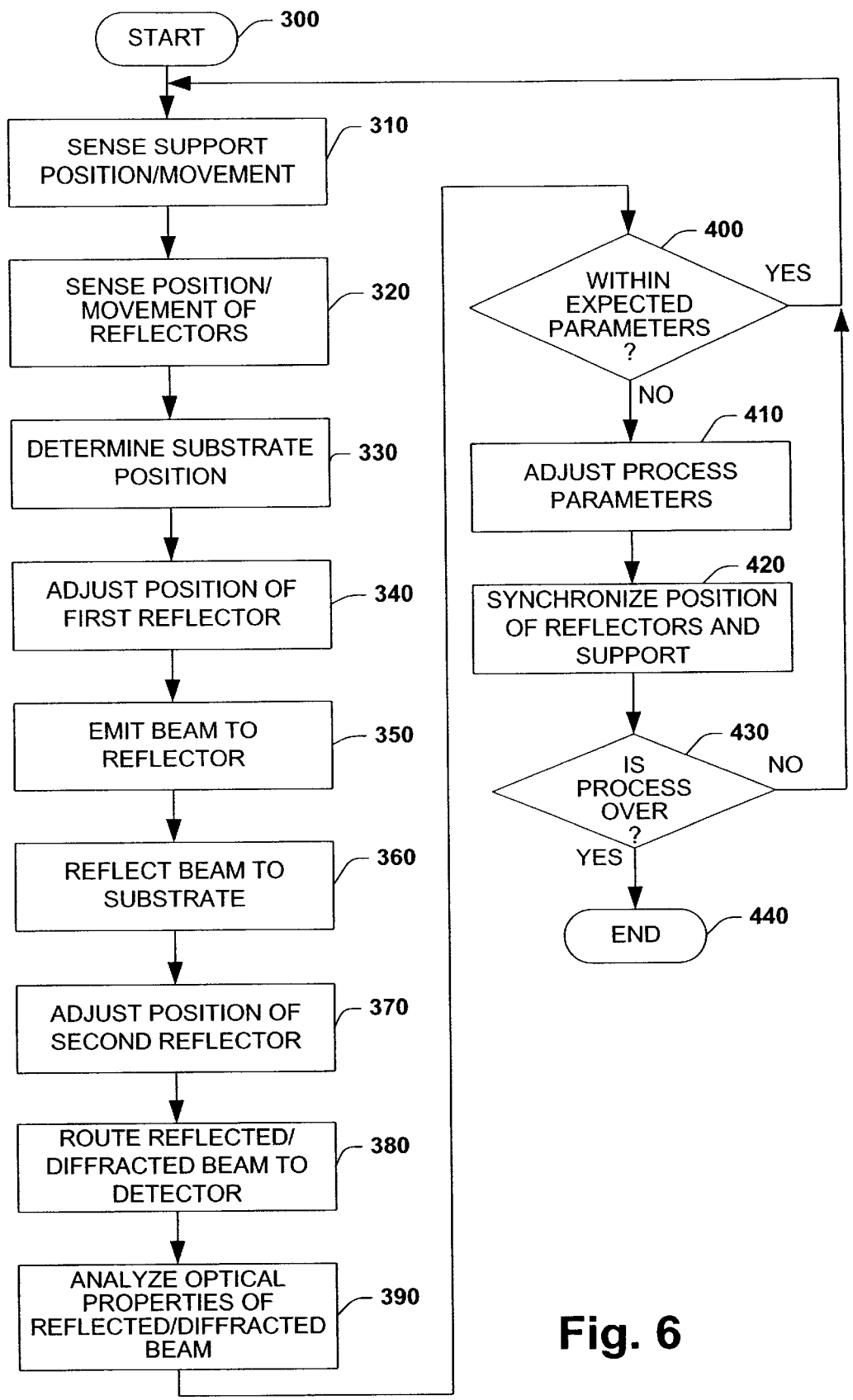
FIG. 6 is a flow diagram illustrating another example of a methodology for monitoring substrate characteristics and implementing process control in accordance with the present invention.

In view of the exemplary systems shown and described above, a methodology, which may be implemented in accordance with the present invention, will be better appreciated with reference to the flow diagrams of FIGS. 5 and 6. While, for purposes of simplicity of explanation, the methodologies of FIGS. 5 and 6 are shown and described as executing serially, it is to be understood and appreciated that the present invention is not limited by the illustrated order, as some aspects can, in accordance with the present invention, occur in different orders and/or concurrently with other aspects from that shown and described herein. Moreover, not all illustrated functionality may be required to implement a methodology in accordance with the present invention.

Turning to FIG. 5, the methodology begins at step 200 in which operating characteristics are initialized to their starting values. This can include, for example, setting initial optical parameters of an incident beam for measuring topographical characteristics of the substrate that has been loaded onto a moveable support in accordance with an aspect of the present invention. After the substrate is appropriately positioned on the support, the support can be activated to rotate or otherwise move the substrate.

At 210, the position and/or movement of the support is sensed. For example, an encoder can monitor movement of the support and provide a signal indicative of the position and/or velocity of the rotating support.

At 220, an indication of the position and/or movement of a reflector is sensed. The reflector is arranged to receive light emitted from a light source and redirecting the light beam onto the substrate. Next, at 230, the substrate position is determined, such as based on the sensed position and/or movement of the substrate support. Because the position of the substrate relative to the support is known, the position of selected parts of the substrate also can be determined based on the position of the support.

At 240, the position of the reflector is adjusted based on the determined substrate position. For example, the reflector is coupled to a motor or other device operative to move the mirror about one or more axes. The motor is controlled to adjust the position of the mirror so that the light beam is emitted (250), the beam is reflected (260) by the reflector to strike a desired part of the moving substrate. The incident beam is reflected and diffracted to provide a beam having optical properties that are functionally related to the topographical features of the substrate. Accordingly, at 270, the reflected and/or diffracted beam is detected, which detected beam can used to discern optical properties of the substrate. The optical properties of the substrate can, in turn, be employed to determine topographical features of the substrate, such as its thickness, thickness of layers on the substrate, and the like.

At 280, a determination is made as to whether the associated methodology has completed. If the determination is negative, indicating additional processing and/or sensing is desired, the methodology returns to 210. If the process has completed, the methodology ends at 290.

While the methodology of FIG. 5 illustrates discrete actions, such actions are interdependent. That is, feedback from various sensors (210, 220) can be used to synchronize the interrogation of the substrate by the reflected light beam (270) with movement of its support platform. For example, the reflector position can be continually adjusted based on the substrate position, which varies commensurately with rotation of its support. As a result, the reflected beam incident on the substrate selectively interrogates a given part of the substrate while it moves, such that desired information can be determined for selected parts of the substrate FIG. 6 illustrates another methodology that can be implemented in accordance with an aspect of the present invention. The process begins at step 300 in which operating characteristics are initialized to their starting values. This may include, for example, loading a substrate onto a support, initiating rotation of a support, setting initial optical parameters (e.g., intensity and wavelength(s)) of an incident beam, and/or controlling other initial process parameters associated with fabrication of the substrate in accordance with an aspect of the present invention.

At 310, the position and/or movement of the support is sensed. For example, an encoder can monitor movement of the support and provide a signal indicative of the position and/or velocity of the rotating support.

At 320, an indication of the position and/or movement of a first reflector is sensed. The first reflector is arranged to receive light emitted from a light source and to redirect the light beam onto the substrate. In particular, the first reflector is coupled to a motor or other device operative to move the mirror about one or more axes. The motor can be controlled to adjust the position of the mirror in accordance with an aspect of the present invention. At 330, the substrate position is determined, such as based on the sensed position and/or movement of the substrate support. Because the position of the substrate relative to the support is known, the position of selected parts of the substrate also can be determined based on the position of the support.

At 340, the position of the first reflector is adjusted based on the determined substrate position. For example, the position of the reflector is adjusted so that that as a light beam emitted (350) on to the reflector, the beam is reflected (360) to provide an incident beam that strikes a desired part of the moving substrate. In one aspect, the reflector position can be repeatedly adjusted based on the position of the substrate so that the incident beam selectively interrogates a same or different parts of the moving substrate. The incident beam is reflected and/or diffracted to provide a beam having optical properties that are functionally related to the topographical features of the substrate.

The reflected and/or refracted beam is provided to a second reflector. At 370, the position of the second reflector is adjusted based on the position of the substrate to route the beam to a detector. For example, the detector can be an analyzer equipped with a spectrometer or other equipment operative to discern optical properties of the beam. At 390, the optical properties of the reflected and/or diffracted beam are analyzed, such as by generating a signature profile based on the optical properties of the reflected and/or diffracted beam and comparing the generated signature with a signature library. The optical properties are indicative of the optical properties of the substrate. The optical properties of the substrate can, in turn, be employed to determine topographical features of the substrate, such as its thickness, thickness of layers on the substrate, and the like. It is to be understood and appreciated that the foregoing functionality (310–390) can be implemented during processing of the substrate, such as when a coating, film, solvent, or other material is being applied to the substrate.

At 400, a determination is made as to whether the sensed parameters indicate that the associated process is operating within expected parameters. For example, by determining thickness of film being applied at a plurality of locations on the substrate surface, the uniformity of the thickness can be evaluated and voids or defects can be detected. In addition, such an evaluation also can be used to detect other defects associated with the application of materials onto the substrate. If the determination at 400 is negative, indicating that the detected substrate and/or process characteristics are not within expected parameters, the methodology proceeds to 410.

At 410, process parameters can be adjusted based on the characteristics of the substrate determined from the reflected and/or diffracted beam. The process parameters, for example, can include the rate at which materials are being applied on to the substrate, the rate of rotation of the substrate, the optical characteristics of the beam being emitted on to the substrate, temperature, pressure, and the like. Next at 420, the position and/or movement of the first and second reflectors are synchronized with the position and/or movement of the substrate support. Such synchronization can be implemented based on position and/or velocity information detected for the reflectors and support.

At 430, a determination is made as to whether the process has completed. If the process has not completed, the process returns to 310. Similarly, if the determination at 400 indicates that the detected substrate and process characteristics are within expected operating parameters, the methodology returns to 310. After the process is completed, such as after a layer of a desired thickness has been applied to or removed from the substrate, the process ends at 440.

In view of the foregoing, it will be appreciated that the present invention facilitates improving semiconductor integrity and reliability by ensuring desired substrate parameters during processing while a substrate is moving. In addition, process parameters can be adjusted in situ to further increase quality and accuracy during fabrication.

What has been described above includes exemplary implementations of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for measuring characteristics of a substrate, comprising:
    a positioning system having a support for receiving a substrate, the positioning system being operable to move the substrate supported thereby;
    a measurement system having a source that emits a beam onto a moveable reflector, which reflects an incident beam to the substrate, the reflector can be rotated about three axes;
    a detector that detects at least one of reflected and diffracted beam from the substrate; and
    a control system that controls movement of the reflector as a function of movement of the support so as to selectively interrogate the substrate.

2. The system of claim 1, the moveable reflector defining a first moveable reflector, the system further comprising a second moveable reflector, the control system controlling movement of the second moveable reflector as a function of movement of the support so as to route the at least one of reflected and diffracted beam to the detector.

3. The system of claim 2, the source further comprising a light source, the detector further comprising a spectrometer, the spectrometer providing a signal indicative of substrate characteristics illuminated by the incident beam.

4. The system of claim 3, the support being operative to rotate the substrate and the control system being operative to synchronize operation of the first and second moveable reflectors with the rotation of the substrate such that the incident beam selectively interrogates the substrate as a function of rotation of the substrate.

5. The system of claim 4, further including an application system operatively coupled with the control system for applying material onto the substrate.

6. The system of claim 5, the control system being operable to adjust operating characteristics associated with at least one of the positioning system, the application system, the first reflector, and the second reflector based on the signal indicative of substrate characteristics.

7. The system claim 2, further comprising a first motor operatively connected to move the first reflector relative to at least one axis and a second motor operative connected to move the second reflector relative to at least one axis, the control system controlling activation of the first and second motors as a function of movement of the support.

8. A system for measuring characteristics of a substrate, comprising:
    a support that supports the substrate for movement within a processing chamber;
    a light source operative to emit a beam;
    reflector, adjustable in at least three axes, associated with the light source that receives the beam and reflects the beam as an incident beam on to the substrate, the incident beam interacting with the substrate to provide at least one of reflected and diffracted light having optical properties based on characteristics of the substrate;

an analyzer that receives the at least one of reflected and diffracted light and to determine optical properties of the substrate; and a control system that controls movement of the reflector associated with the light source as a function of movement of the substrate, such that the incident beam selectively interrogates the substrate.

9. The system of claim 8, wherein the support is operable to rotate the substrate.

10. The system of claim 9, further comprising an adjustable reflector associated with the analyzer and operative to receive the at least one of reflected and diffracted light, the control system being operative to control movement of the adjustable reflector associated with the analyzer, such that the at least one of reflected and diffracted light is routed to the analyzer.

11. The system of claim 10, the analyzer further comprising a spectrometer, the spectrometer providing to the control system a signal indicative of optical characteristics of parts of the substrate illuminated by the incident beam based on the at least one of reflected and diffracted light.

12. The system of claim 11, the control system controlling movement of the reflector associated with the light source and the reflector associated with tile analyzer to be in synchronization with rotation of the substrate, such that the incident beam selectively interrogates the substrate as a function of rotation of the substrate and the at least one of reflected and diffracted light is routed to the analyzer.

13. The system of claim 11, further comprising an application system coupled with the control system and operative to apply material onto the substrate during a fabrication process.

14. The system of claim 13, the control system being operative to adjust operating characteristics associated with at least one of the support, the application system, the reflector associated with the light source, and the reflector associated with the analyzer based on the signal indicative of substrate characteristics.

15. A system for measuring characteristics of a substrate, comprising:

means for rotating a substrate within a processing environment;

means for emitting an incident light beam;

means for adjustably reflecting the emitted light beam in at least three axes to a selected location of the substrate, which produces at least one of reflected and diffracted light;

means for analyzing optical properties of the at least one of reflected and diffracted light; and means for controlling the means for reflecting to reflect the emitted light beam based on movement of the substrate.

16. The system of claim 15 further comprising means for adjustably routing the at least one of reflected and diffracted light to a means for collecting, the means for controlling the means for adjustably routing to route the at least one of reflected and diffracted light based on movement of the substrate.

17. The system of claim 16, further comprising means for applying material on the substrate, the control system controlling the means for applying based on the optical properties of the at least one of reflected and diffracted light.

18. A method for measuring characteristics of a substrate, comprising the steps of:

moving a substrate supported within a processing environment;

emitting an incident light beam onto a reflector;

adjusting orientation of the reflector in at least three axes based on the moving of the substrate to selectively direct the incident beam on to a surface of the substrate; and receiving at least one of reflected and diffracted light in response to interaction of the incident beam with the substrate, the at least one of reflected and diffracted light having optical properties indicative of substrate characteristics.

19. The method of claim 18, the moving further comprising rotating the substrate and the adjusting orientation further varying as a function of rotation of the substrate.

20. The method of claim 19, further comprising adjustably reflecting the at least one of reflected and diffracted light to an analyzing apparatus that receives the at least one of reflected and diffracted light and determines optical properties thereof.

21. The method of claim 20, further comprising applying material on to the substrate while the substrate is rotating in the processing environment.

22. The method of claim 21, further comprising controlling the applying of material based on the determined optical properties of the at least one of reflected and diffracted light.

23. The method of claim 20, further comprising controlling the adjusting orientation of the reflector and the adjustably reflecting, based on the moving of the substrate to selectively interrogate different parts of the substrate and to facilitate a determination of substrate characteristics based on the at least one of reflected and diffracted light for the different parts.

* * * * *

UNITED STATES PATENT AND TRADEMARK OFFICE
CERTIFICATE OF CORRECTION

PATENT NO.     : 6,704,101 B1
DATED          : March 9, 2004
INVENTOR(S)    : Bharath Rangarajan et al.

It is certified that error appears in the above-identified patent and that said Letters Patent is hereby corrected as shown below:

Column 1,
Line 20, replace "comers" with -- corners --

Column 13,
Line 3, delete the second instance of "that"
Line 4, replace "beam emitted" with -- beam is emitted --

Signed and Sealed this

Twenty-ninth Day of June, 2004

JON W. DUDAS
*Acting Director of the United States Patent and Trademark Office*